United States Patent [19]

Gadek et al.

[11] 4,104,308

[45] Aug. 1, 1978

[54] SYNTHESIS OF SQUARIC ACID

[75] Inventors: Thomas Richard Gadek; David Berhard Sclove; Robert Lee Vollmer, all of Boulder, Colo.

[73] Assignee: International Business Machines Corporation, Armonk, N.Y.

[21] Appl. No.: 698,614

[22] Filed: Jun. 21, 1976

[51] Int. Cl.$^2$ ............... C07C 45/00; C07D 295/06
[52] U.S. Cl. ............... 260/586 R; 544/106; 544/175
[58] Field of Search ............... 260/586 R, 247.7 K, 260/247

[56] References Cited

U.S. PATENT DOCUMENTS

| 3,059,030 | 10/1962 | Park et al. | 260/586 R |
| 3,833,489 | 9/1974 | Ercoli et al. | 260/586 R |

FOREIGN PATENT DOCUMENTS 1,568,291  3/1970  Fed. Rep. of Germany ...... 260/586 R

OTHER PUBLICATIONS

Maahs, "Angew. Chem", vol. 75, p. 982 (1963).
Maars et al., "Angew. Chem. Internat. Edit", vol. 5, (1966), No. 10, pp. 888–893.

*Primary Examiner*—Norman Morgenstern
*Attorney, Agent, or Firm*—Joseph G. Walsh

[57] ABSTRACT

Squaric acid is prepared by reacting hexachlorobutadiene with an excess of morpholine in the presence of an aromatic hydrocarbon solvent while maintaining the temperature between 110° C and 120° C, and then converting the resulting 1,1,3-trichloro-2,4,4-trimorpholino-butadiene to 3-morpholinotrichloro-2-cyclobuten-1-one, which in turn is hydrolyzed in the presence of strong acid to produce the desired squaric acid.

5 Claims, No Drawings

SYNTHESIS OF SQUARIC ACID

FIELD OF THE INVENTION

The present invention is concerned with an improved process for the preparation of squaric acid. The systematic chemical name for squaric acid is 3,4-dihydroxy-3-cyclobutene-1,2-dione. By careful control of the reaction conditions, the process of the present invention results in an increased yield of purer product than previously obtained. In addition, the present process avoids violent highly exothermic decomposition of the starting materials such as may occur using the prior art methods.

PRIOR ART

Squaric acid has been known for some time and the literature contains several methods for its synthesis. In particular, the prior art describes a process beginning with the same starting materials as the process of the present invention. German Patent OS 1,568,291, and also the publication by G. Maahs in Agnew Chem., 75, 982(1963), both describe a process for the production of squaric acid beginning with the starting materials of the process of the present invention, namely hexachlorobutadiene and morpholine. The prior art describes the reaction of these materials, with morpholine being present in a large excess, for example a molar ratio of from about 8 to 1 to about 12 to 1. The prior art teaches that the materials are heated together for several hours at a temperature of from 60° to 100° C. The prior art teaches that it is then advisable to remove the by-products before proceeding with additional steps. According to the process of the present invention, the reaction of the hexachlorobutadiene and excess morpholine, preferably at a molar ratio of about 6 to 1, is carried out in the presence of an aromatic hydrocarbon solvent and at a temperature carefully controlled and maintained between 110° C and 120° C. When the reaction is carried out in the presence of the aromatic hydrocarbon solvent and under the correctly controlled temperature, explosions are avoided. Furthermore, there is no need to remove any by-products. It should, in fact, be specifically mentioned that it is one of the advantages of the present process that it can be carried out in a single reaction vessel, with no need to remove by-products or transfer the reactants.

The reaction of hexachlorobutadiene and morpholine produces 1,1,3-trichloro-2,4,4-trimorpholinobutadiene. The prior art describes the conversion of this material to 3-morpholinotrichloro-2-cyclobuten-1-one. In the prior art this is accomplished by bringing the pH to within the range of 6 to 8 and stirring the solution for several hours at a temperature of from about 50° C to about 75° C. We have now found that it is unexpectedly advantageous if this step is carried out in the presence of a buffer which maintains the pH; and that the pH can be set within the range of from about 4.0 to about 7.0. When the reaction is carried out in accordance with the teaching of the prior art using an unbuffered solution, the major product is a compound which cannot be converted into the desired squaric acid under the conditions of the final step. The presence of the buffer prevents the formation of this undesired compound.

The final step in the synthesis, both as reported in the prior art and as carried out in the present invention, is the hydrolysis of 3-morpholinotrichloro-2-cyclobuten-1-one to squaric acid by treatment with strong acid under reflux.

SUMMARY OF THE INVENTION

As discussed above, the present invention differs from the prior art in that the first step of the synthesis is carried out in the presence of an aromatic hydrocarbon solvent and at a carefully controlled temperature maintained between 110° C and 120° C. Toluene is the preferred aromatic hydrocarbon solvent. Other useful materials include ethylbenzene, the xylenes and mixtures of such materials. Benzene (on reflux) may also be used, but the lower reaction temperature is less advantageous.

Another feature distinguishing the present invention from the prior art is the use of a buffered system during the conversion of the 1,1,3-trichloro-2,4,4-trimorpholinobutadiene into 3-morpholinotrichloro-2-cyclobuten-1-one. This step is carried out, preferably at about 60° C, with the pH between about 4.0 and about 7.0. Excellent results have been obtained using a pH of 4.8 with a buffer comprising sodium acetate and acetic acid. The mixture is preferably stirred under these conditions for about 16 hours.

Strong acid is required for the last step, which is the hydrolysis of the 3-morpholinotrichloro-2-cyclobuten-1-one to squaric acid. Satisfactory results have been obtained with hydrochloric acid and also with sulphuric acid.

The squaric acid produced by the process of the present invention is sufficiently pure to be used, without additional purification, in the manufacture of squarylium dyes.

The following Example is given to illustrate the preferred embodiment of the process of the present invention. It is given solely for the purposes of illustration and should not be interpreted as a limitation of the scope of the present invention, many variations of which are possible without departing from the spirit or scope thereof.

EXAMPLE 1

Into a 50ml round bottom flask equipped with a reflux condenser, overhead stirrer and a calcium chloride drying tube, are placed hexachlorobutadiene (25g, 0.096mol), morpholine (50ml, 50g, 0.57mol) and toluene (25ml). The mixture is heated with an oil bath at 110°–120° C for a period of 7 hours (reflux). The mixture is allowed to cool, and then a sodium acetate/acetic acid buffer (200ml, pH 4.8, 1.0M HOAc, 1.0 M NaOAc) is added and stirred at 60° C for 16 hours. The mixture is allowed to cool, and then 60ml of concentrated sulfuric acid is added. After the addition of the acid is complete, the mixture is refluxed for 24 hours and then cooled to room temperature. The product is collected by filtration, washed with 50ml of water and 50ml of acetone, then air dried. Yield: 5.01 grams (45.5%, $\lambda$ max = 268 nm, $\epsilon = 2.56 \times 10^4$).

What is claimed is:

1. In a process for the preparation of 3,4-dihidroxy-3-cyclobutene-1,2-dione by the steps of (a) reacting hexachlorobutadiene with an excess of morpholine, the morpholine being present at the start of the reaction in a molar ratio of about 6 to 1 with respect to the hexachlorobutadiene, (b) converting the thus formed 1,1,3-trichloro-2,4,4-trimorpholinobutadiene to 3-morpholinotrichloro-2-cyclobuten-1-one by heating, and (c) hydrolyzing the 3-morpholinotrichloro-2-cyclobuten-1-one to 3,4-dihydroxy-3-cyclobuten-1,2-dione, the improvement according to which the reaction between the hexachlorobutadiene and the morpholine is carried out in the presence of an aromatic hydrocarbon solvent, and at a temperature maintained between 110° C and 120° C, and the conversion of the 1,1,3-trichloro-2,4,-trimorpholinobutadiene to 3,morpholinotrichloro-2-cyclobutene-1-one is carried out in the presence of a buffer at a pH between 4.0 and 7.0.

2. A process as claimed in claim 1 where the entire reaction is carried out in a single reaction vessel.

3. A process as claimed in claim 1 wherein the aromatic hydrocarbon solvent is toluene.

4. A process as claimed in claim 1 wherein the pH is maintained at 4.8.

5. A process as claimed in claim 1 wherein the buffer comprises sodium acetate and acetic acid.

* * * * *